United States Patent
Boucher

(10) Patent No.: US 12,193,757 B2
(45) Date of Patent: Jan. 14, 2025

(54) VARIABLE HEIGHT SUPPORT STRUCTURE

(71) Applicant: INTUITIVE SURGICAL OPERATIONS, INC., Sunnyvale, CA (US)

(72) Inventor: Timothy D. Boucher, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 635 days.

(21) Appl. No.: 17/065,840

(22) Filed: Oct. 8, 2020

(65) Prior Publication Data
US 2021/0121239 A1   Apr. 29, 2021

Related U.S. Application Data

(60) Provisional application No. 62/927,473, filed on Oct. 29, 2019.

(51) Int. Cl.
*A61B 34/20* (2016.01)
*A61B 90/50* (2016.01)
(Continued)

(52) U.S. Cl.
CPC .............. *A61B 34/20* (2016.02); *A61B 90/50* (2016.02); *F16M 11/38* (2013.01); *F16M 13/02* (2013.01);
(Continued)

(58) Field of Classification Search
CPC . Y10T 403/32024; A61B 34/20; A61B 90/50; A61B 2034/2051; A61B 2034/2061; A61B 34/37; A61B 2034/741; A61B 2034/742; A61B 2017/00203; A61B 2017/00477; F16M 2200/061; F16M 2200/063; F16M 11/24
(Continued)

(56) References Cited

U.S. PATENT DOCUMENTS 6,289,187 B1   9/2001  Swift et al.
D606,669 S  *  12/2009  Giorgi ............................. D25/64
(Continued)

FOREIGN PATENT DOCUMENTS

WO    WO-2016191298 A1   12/2016
WO    WO-2018009841 A1   1/2018
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Alfred J Wujciak
(74) *Attorney, Agent, or Firm* — Haynes & Boone, LLP

(57) ABSTRACT

A variable height support structure is provided. The variable height support structure can include a first support member, a second support member, a first expansion link, a second expansion link, and a third expansion link. The variable height support structure can selectively transition from a compressed configuration to an expanded configuration along a longitudinal central axis that extends between the first support member and the second support member.

13 Claims, 13 Drawing Sheets

(51) Int. Cl.
*F16M 11/38* (2006.01)
*F16M 13/02* (2006.01)
*A61B 17/00* (2006.01)
*A61B 34/00* (2016.01)
*A61B 34/35* (2016.01)
*A61B 34/37* (2016.01)

(52) U.S. Cl.
CPC ............ *A61B 2017/00203* (2013.01); *A61B 2017/00477* (2013.01); *A61B 2034/2051* (2016.02); *A61B 2034/2061* (2016.02); *A61B 34/35* (2016.02); *A61B 34/37* (2016.02); *A61B 2034/741* (2016.02); *A61B 2034/742* (2016.02); *F16M 2200/063* (2013.01); *F16M 2200/068* (2013.01)

(58) Field of Classification Search
USPC .......... 248/274.1, 276.1, 288.11, 121, 122.1, 248/125.1, 157, 161, 421
See application file for complete search history.

(56) References Cited

U.S. PATENT DOCUMENTS

| | | | |
|---|---|---|---|
| 7,772,541 B2 | 8/2010 | Froggatt et al. | |
| 7,950,325 B2* | 5/2011 | Kachkovsky | B30B 1/103 |
| | | | 100/285 |
| 7,988,232 B2* | 8/2011 | Weber | B60N 2/508 |
| | | | 384/58 |
| 10,512,515 B2 | 12/2019 | Bailey | |
| 10,639,220 B1* | 5/2020 | Smith | A61G 7/1019 |
| 2006/0165841 A1 | 7/2006 | Golz | |
| 2010/0287808 A1* | 11/2010 | King | F41C 23/02 |
| | | | 42/85 |
| 2018/0170466 A1* | 6/2018 | Enoch | B62D 57/032 |

FOREIGN PATENT DOCUMENTS

| | | |
|---|---|---|
| WO | WO-2018132386 A1 | 7/2018 |
| WO | WO-2018145100 A1 | 8/2018 |
| WO | WO-2019018736 A2 | 1/2019 |
| WO | WO-2019027922 A1 | 2/2019 |

* cited by examiner

VARIABLE HEIGHT SUPPORT STRUCTURE

CROSS-REFERENCE TO RELATED APPLICATIONS

This patent application claims priority to and the benefit of the filing date of U.S. Provisional Application 62/927,473 filed Oct. 29, 2019, which is incorporated by reference herein in its entirety.

FIELD

The present disclosure is directed to a variable height support structure that can transition from a compressed configuration to an expanded configuration.

BACKGROUND

Minimally invasive medical techniques are intended to reduce the amount of tissue that is damaged during interventional procedures, thereby reducing patient recovery time, discomfort, and harmful side effects. Such minimally invasive techniques may be performed through natural orifices in a patient anatomy or through one or more surgical incisions. Physicians may insert minimally invasive medical instruments (including surgical, diagnostic, therapeutic, or biopsy instruments) through these natural orifices or incisions to reach a target tissue location. One such minimally invasive technique is to use a flexible and/or steerable elongate device, such as a flexible catheter, that can be inserted into anatomic passageways and navigated toward a region of interest within the patient anatomy. Control of such an elongate device by medical personnel involves the management of several degrees of freedom including at least the management of insertion and retraction of the elongate device as well as steering of the device. In addition, different modes of operation may also be supported.

Robot-assisted interventional systems may be used to insert the flexible interventional instruments into the patient anatomy. Several interventional instruments are made of flexible material that allows for maneuverability through a patient's body. At least a portion of the interventional instrument extending between the patient and a robot-assisted manipulator may be unsupported, and the flexible nature of the instrument can cause it to bend, twist, or buckle in an undesirable manner at a point external to the patient's body when force is exerted to insert the instrument into the patient's anatomy. Deformation of the instrument may damage internal components such as optical fiber shape sensors or endoscopic equipment. Adequate structure may also be needed to allow for insertion control of interventional instruments.

BRIEF SUMMARY

In one aspect, a variable height lateral support is provided. The variable height lateral support can be capable of a high expansion ratio to allow large axial motions. For example, the variable height lateral support can utilize a truss structure and can efficiently stow to a small axial package that can deploy in an axial motion. The variable height lateral support can provide a variable length channel for a flexible member to pass through.

In an aspect, a variable height support structure can include a first support member connected to a first joint, a second joint, and a third joint, a second support member connected to a fourth joint, a fifth joint, and a sixth joint, a first expansion link connected to the first joint and the fourth joint, a second expansion link connected to the second joint and the fifth joint, and a third expansion link connected to the third joint and the sixth joint. The variable height support structure can selectively transition from a compressed configuration to an expanded configuration along a longitudinal central axis that extends between the first support member and the second support member.

The variable height support structure can include a two-axis gimbal such that the two-axis gimbal rotates relative to the first support member along a longitudinal axis parallel to the longitudinal central axis and the first expansion link rotates about the two-axis gimbal along a transverse axis. The second joint can include a second two-axis gimbal such that the second two-axis gimbal rotates relative to the first support member along a second longitudinal axis parallel to the longitudinal central axis and the second expansion link rotates about the second two-axis gimbal along a second transverse axis. The third joint can include a third two-axis gimbal such that the third two-axis gimbal rotates relative to the first support member along a third longitudinal axis parallel to the longitudinal central axis and the third expansion link rotates about the third two-axis gimbal along a third transverse axis. In an aspect, the first joint can include an axle to connect the two-axis gimbal to the first support member and the axle can extend along the longitudinal axis. The variable height support structure can have an expansion ratio of approximately 6.5 to 1.

In an aspect, movement of the first support member, second support member, first expansion link, second expansion link, and third expansion link can be constrained by a single degree of freedom along the longitudinal central axis.

In another aspect, the variable height support structure can include a third support member connected to a seventh joint, an eighth joint, and a ninth joint, a fourth expansion link connected to the fourth joint and the seventh joint, the fourth expansion link including a fourth link recessed surface at an end of the fourth expansion link connected to the fourth joint, a fifth expansion link connected to the fifth joint and the eighth joint, and a sixth expansion link connected to the sixth joint and the ninth joint. The first expansion link can include a first link recessed surface at an end of the first expansion link connected to the fourth joint such that the first link recessed surface is adjacent to the fourth link recessed surface along a transverse axis.

In a further aspect, the first support member can include a central aperture configured to receive a flexible elongate device. The central aperture can have a center on the longitudinal central axis. The central aperture can include a chamfered lumen configured to receive the flexible elongate device and to provide lateral support to the flexible elongate device.

In another aspect, the variable height support structure can include a coupler configured to couple the variable height support structure to an instrument manipulator.

In another aspect, an apparatus can include a variable height support structure. The variable height support structure can include a first support member connected to a first gimbal, a second gimbal, and a third gimbal. The first support member can include a first aperture configured to an elongated flexible instrument. The variable height support structure can include a second support member connected to a fourth gimbal, a fifth gimbal, and a sixth gimbal. The second support member can include a second aperture configured to receive the elongated flexible instrument. The first aperture can have a center on a longitudinal axis that extends between the first support member and the second support member. The second aperture can have a center on the longitudinal axis. The variable height support structure can also include a first expansion link connected to the first gimbal and the fourth gimbal, a second expansion link connected to the second gimbal and the fifth gimbal, and a third expansion link connected to the third gimbal and the sixth gimbal, and a coupler configured to couple the variable height support structure to an instrument manipulator. The variable height support structure can selectively transition from a compressed configuration to an expanded configuration along the longitudinal axis. In an aspect, the first gimbal can rotate relative to the first support member along a first longitudinal axis and the first expansion link can rotate about the first gimbal along a first transverse axis. The first longitudinal axis can be parallel to the longitudinal axis. The second gimbal can rotate relative to the first support member along a second longitudinal axis and the second expansion link can rotate about the second gimbal along a second transverse axis. The second longitudinal axis can be parallel to the longitudinal axis. The third gimbal can rotate relative to the first support member along a third longitudinal axis and the third expansion link can rotate about the third gimbal along a third transverse axis. The third longitudinal axis can be parallel to the longitudinal axis.

In an aspect, the apparatus can include an axle to connect the first gimbal to the first support member. The axle can extend along the longitudinal axis. The apparatus can include a bearing to connect the first gimbal to the first expansion link. In an aspect, the variable height support structure can have an expansion ratio of approximately 6.5 to 1. In another aspect, movement of the first support member, second support member, first expansion link, second expansion link, and third expansion link can be constrained by a single degree of freedom along the longitudinal central axis.

In another aspect, the variable height support structure can include, a third support member connected to a seventh gimbal, an eighth gimbal, and a ninth gimbal, a fourth expansion link connected to the fourth gimbal and the seventh gimbal, the fourth expansion link including a fourth link recessed surface at an end of the fourth expansion link connected to the fourth gimbal, a fifth expansion link connected to the fifth gimbal and the eighth gimbal, and a sixth expansion link connected to the sixth gimbal and the ninth gimbal. The first expansion link can include a first link recessed surface at an end of the first expansion link connected to the fourth gimbal such that the first link recessed surface is adjacent to the fourth link recessed surface along a transverse axis.

In another aspect, the first aperture can include a first chamfered lumen configured to receive the elongated flexible instrument. The second aperture can also include a second chamfered lumen for receiving the elongated flexible instrument. The apparatus can also include a proximal coupler configured to couple the variable height support structure to a proximal portion of the instrument manipulator. The apparatus can include a distal coupler configured to couple the variable height support structure to a distal portion of the instrument manipulator.

In an aspect, the first gimbal can be a two-axis gimbal. In another aspect, the fourth gimbal can be a two-axis gimbal. In an aspect, one or more of the first gimbal, second gimbal, third gimbal, fourth gimbal, fifth gimbal, and sixth gimbal can be a two-axis gimbal.

Further features and advantages of embodiments described herein, as well as the structure and operation of the various embodiments, are described in detail below with reference to the accompanying drawings. It is noted that examples described herein are not limited to the specific embodiments described below. Such embodiments are presented herein for illustrative purposes only. Additional embodiments will be apparent to a person skilled in the relevant art(s) based on the teachings contained herein.

BRIEF DESCRIPTION OF THE DRAWINGS/FIGURES

The accompanying drawings, which are incorporated herein and form part of the specification, illustrate embodiments of the present invention and, together with the description, further serve to explain the principles of the invention and to enable a person skilled in the relevant art(s) to make and use the invention.

Features and advantages of the embodiments will become more apparent from the detailed description set forth below when taken in conjunction with the drawings, in which like reference characters identify corresponding elements throughout.

DETAILED DESCRIPTION OF THE INVENTION

The present invention(s) will now be described in detail with reference to embodiments thereof as illustrated in the accompanying drawings. References to "one embodiment", "an embodiment", "an illustrative embodiment", etc., indicate that the embodiment described may include a particular feature, structure, or characteristic, but every embodiment might not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

This disclosure describes various instruments and portions of instruments in terms of their state in three-dimensional space. As used herein, the term position refers to the location of an object or a portion of an object in a three-dimensional space (e.g., three degrees of translational freedom along Cartesian x-, y-, and z-coordinates). As used herein, the term orientation refers to the rotational placement of an object or a portion of an object (e.g., one or more degrees of rotational freedom, such as roll, pitch, and yaw). As used herein, the term pose refers to the position of an object or a portion of an object in at least one degree of translational freedom and to the orientation of that object or portion of the object in at least one degree of rotational freedom (e.g., up to six total degrees of freedom). As used herein, the term shape refers to a set of poses, positions, or orientations measured along an object.

Figure 1:
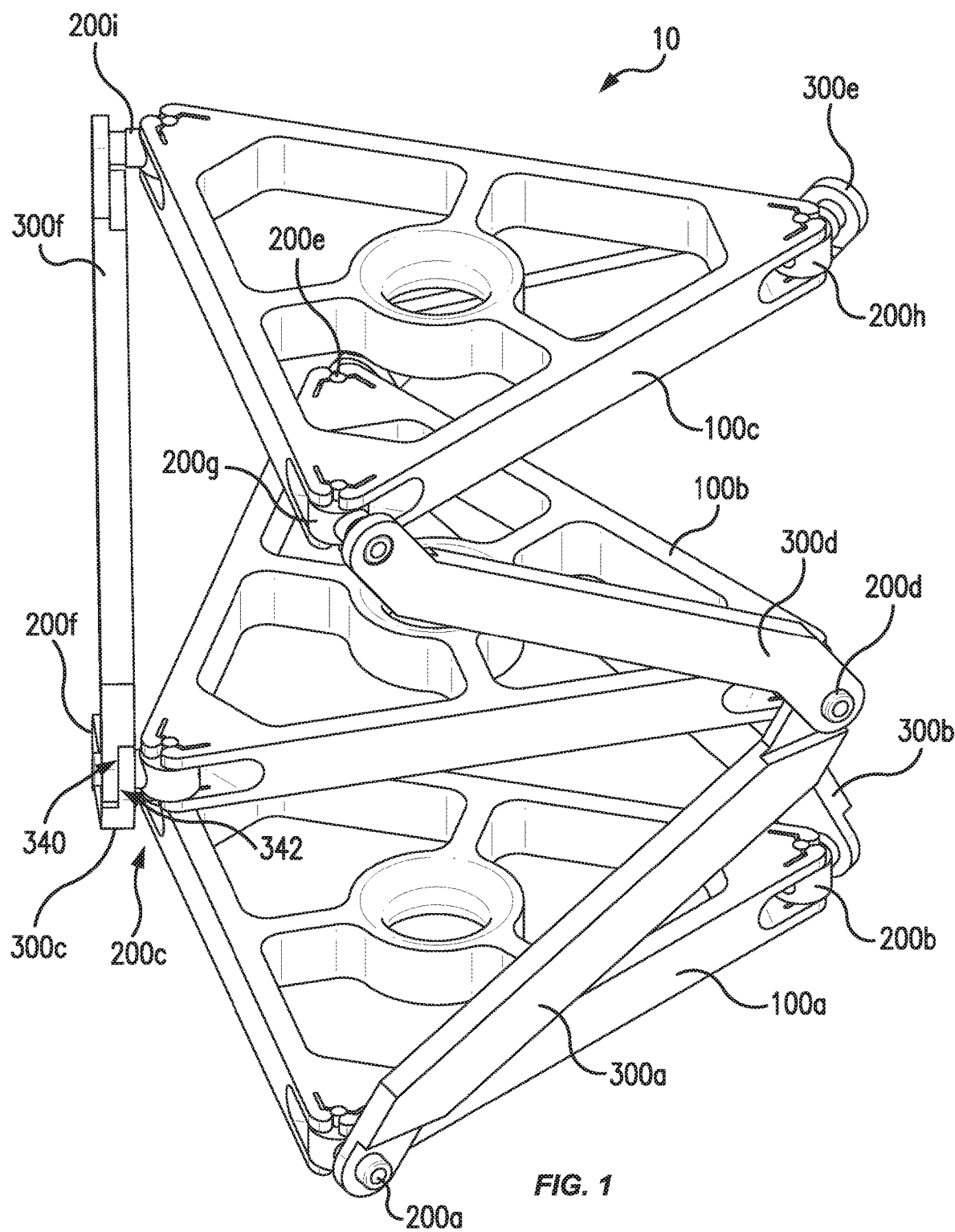
FIG. 1 is a perspective view of a variable height support structure.

Variable height support structure 10 is shown in FIG. 1. Variable height support structure 10 can include support members 100, such as support members 100a-c, joints 200, such as joints 200a-i, and expansion links 300, such as expansion links 300a-f. In an aspect, variable height support structure 10 can include two or more support members 100, six or more joints 200, and three or more expansion links 300. Variable height support structure 10 can have a single degree of freedom and can permit movement in the longitudinal direction. For example, the arrangement of support members 100, joints 200, and expansion links 300 synchronizes the movement of the respective components to each other such that support members 100, joints 200, and expansion links 300 move at the same time, as described further below. For example, movement of any of support members 100, joints 200, or expansion links 300 causes simultaneous movement of the connected support members 100, joints 200, and expansion links 300 due to single degree of freedom arrangement. Variable height support structure 10 can selectively transition from a compressed configuration where adjacent support members abut each other (FIG. 9) to an expanded configuration (FIG. 10), as discussed further below. Variable height support structure 10 can resist movement in the transverse direction. For example, variable height support structure 10 can be laterally stiff to provide lateral support, while permitting longitudinal expansion. FIG. 1 shows the variable height support structure 10 in a partially expanded configuration.

In an aspect, variable height support structure 10 can include a first support member 100a that can be connected to a first joint 200a, a second joint 200b, and a third joint 200c. A second support member 100b can be connected to a fourth joint 200d, a fifth joint 200e, and a sixth joint 200f. Expansion link 300a can be connected to first joint 200a and fourth joint 200d. Expansion link 300b can be connected to second joint 200b and fifth joint 200e. Expansion link 300c can be connected to third joint 200c and sixth joint 200f. The connection between the respective support members 100a-b, joints 200a-f, and expansion links 300a-c can cause simultaneous movement of the connected support members 100a-b, joints 200a-f, and expansion links 300a-c due to the single degree of freedom arrangement. Variable height support structure 10 can selectively transition from a compressed configuration where support member 100a abuts support member 100b to an expanded configuration where support member 100a is longitudinally spaced from support member 100b.

In an aspect, the variable height support structure 10 can include a third support member 100c that can be connected to a seventh joint 200g, an eighth joint 200h, and a ninth joint 200i. An expansion link 300d can be connected to fourth joint 200d and seventh joint 200g. An expansion link 300e can be connected to a fifth joint 200e and an eighth joint 200h. An expansion link 300f can be connected to a sixth joint 200f and a ninth joint 200i. The connection between the respective support members 100a-c, joints 200a-i, and expansion links 300a-f can cause simultaneous movement of the connected support members 100a-c, joints 200a-i, and expansion links 300a-g due to the single degree of freedom arrangement.

Variable height support structure 10 can selectively transition from a compressed configuration to an expanded configuration. In the compressed configuration, support member 100a can abut support member 100b, and support member 100b can abut support member 100c. Alternatively, there may be a small gap between support member 100a and support member 100b and support member 100b and support member 100c in the compressed configuration. In the expanded configuration, support member 100a is longitudinally spaced from support member 100b, and support member 100b is longitudinally spaced from support member 100c. In an aspect, the longitudinal distance between support member 100a and support member 100b can be equal to the longitudinal distance between support member 100b and support member 100c in the compressed configuration and in the expanded configuration.

In another aspect, variable height support structure 10 can include additional support members 100 (e.g., more than three support members), joints 200, and expansion links 300 as desired to satisfy a desired expansion length.

Figure 2:
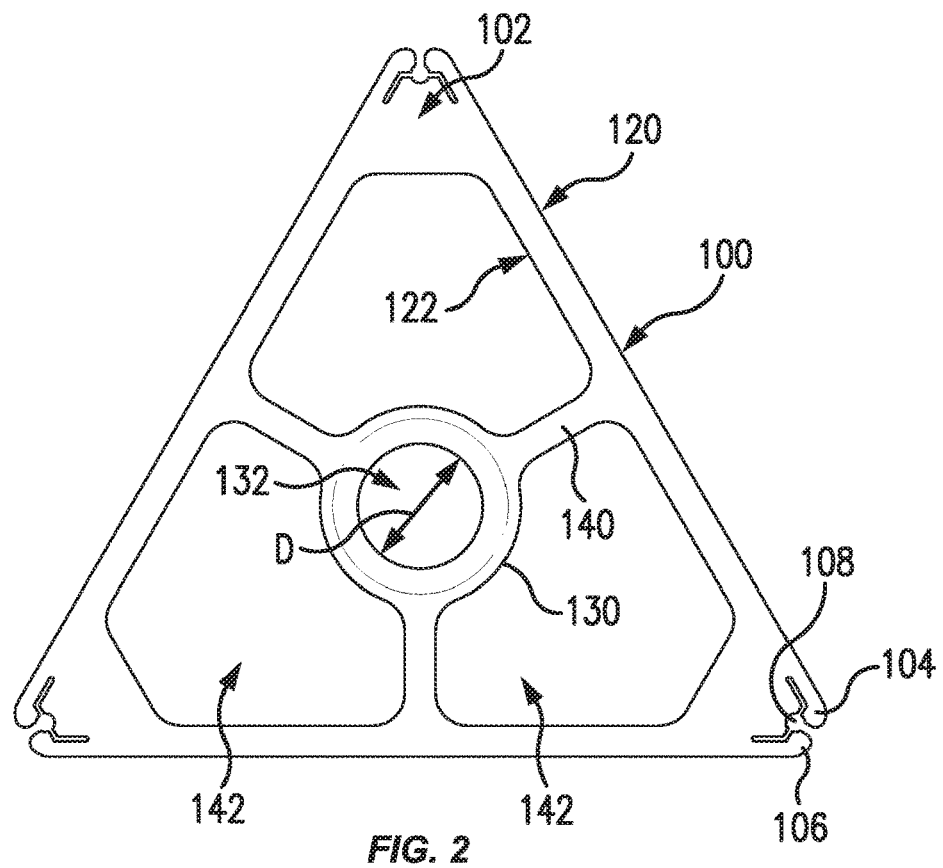
FIG. 2 is a top view of a support member for a variable height support structure.
Figure 3:
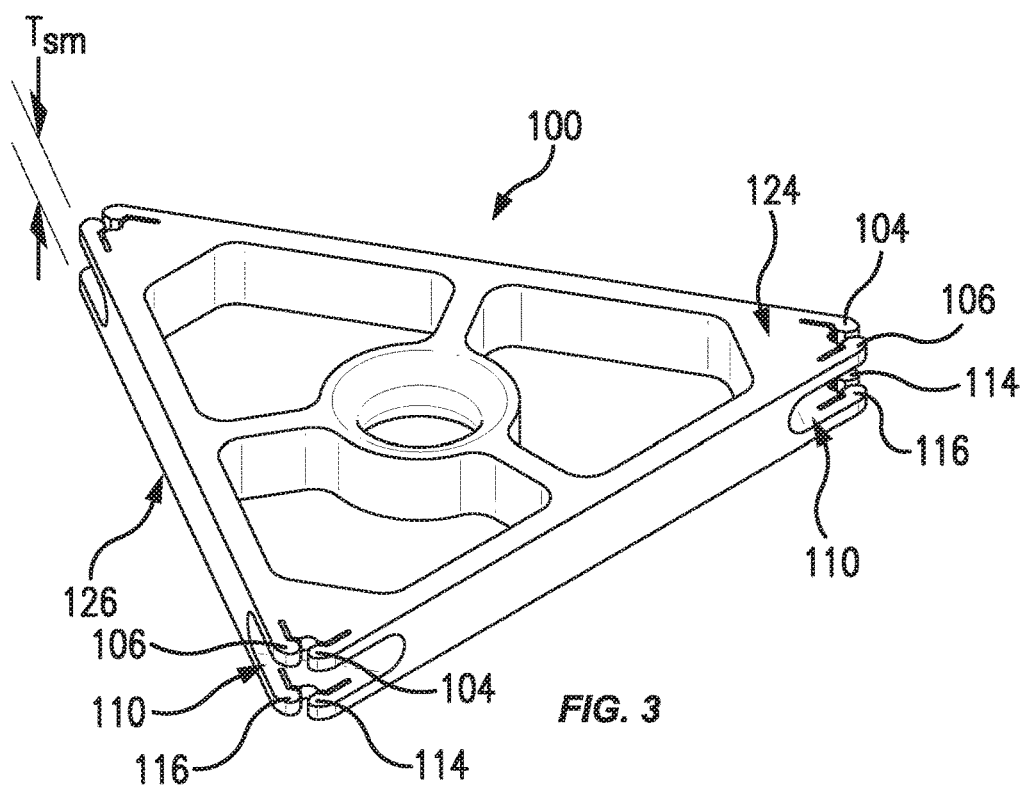
FIG. 3 is a perspective view of the support member of FIG. 2.

Referring now to FIGS. 2-3, support member 100 is shown. Each of support members 100a-c (and other support members) can have a structure as shown in FIGS. 2-3 with respect to support member 100, and as described below. Support member 100 can include ends 102. Ends 102 are positioned outward from a center of support member 100. Ends 102 can be adjacent joints, such as joints 200. An outermost portion of ends 102 can include an upper left frame 104, an upper right frame 106, a lower left frame 114, and a lower right frame 116. Upper frames 104, 106 and lower frames 114, 116 can surround an end cavity 110. In an aspect, end cavity 110 can extend transversely inward and can receive a portion of a joint, such as joint 200.

Figure 4:
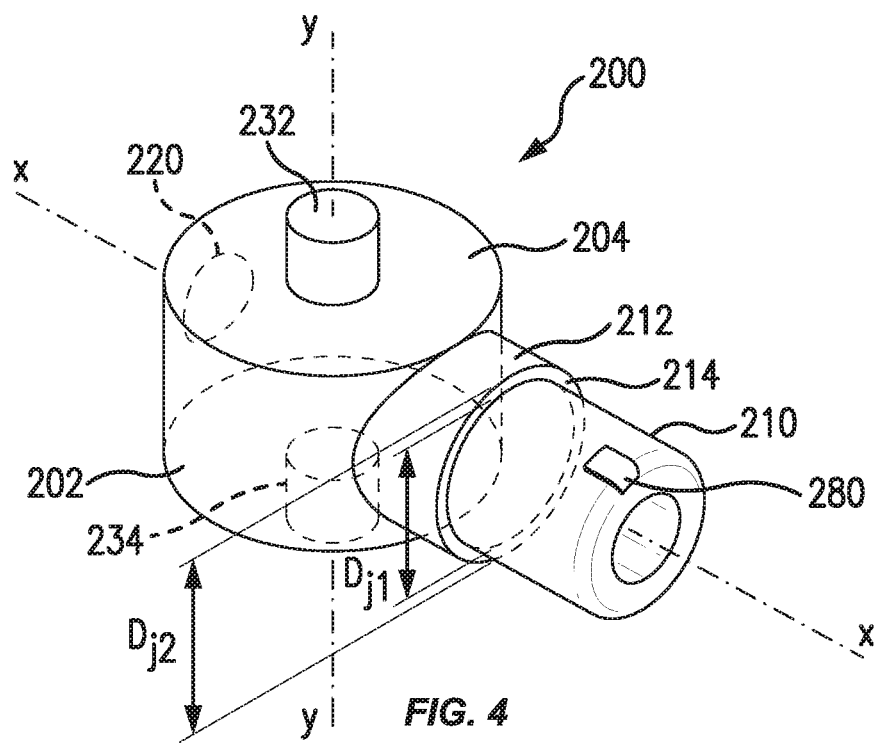
FIG. 4 is a front perspective view of a joint for a variable height support structure.
Figure 5:
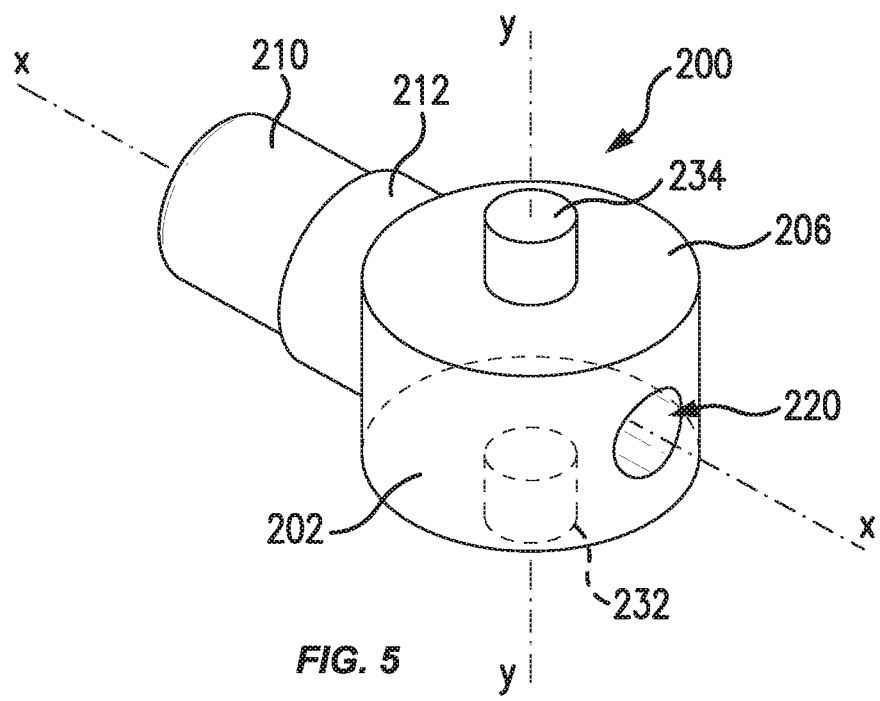
FIG. 5 is a rear perspective view of the joint of FIG. 4.

End 102 can also include a joint aperture 108 to receive a connection to a joint, such as joint 200. For example, joint aperture 108 can receive an axle to connect to a joint, such as upper axle 232 and lower axle 234 of joint 200 (FIGS. 4-5). In this aspect, the connection between joint aperture 108 and joint 200 can be a pin connection to rotatably fix support member 100 to joint 200.

In an aspect, an end of upper left frame 104 can be spaced from upper right frame 106 to allow a joint axle to slide between the respective frames into joint aperture 108 during assembly of variable height support structure 10, for example in a snap fit configuration. Similarly, an end of lower left frame 114 can be spaced from lower right frame 116 to allow a joint axle to slide between the respective frames into joint aperture 108 during assembly of variable height support structure 10, for example in a snap fit configuration. In this aspect, the connection between joint aperture 108 and joint 200 can be a pin connection to rotatably fix support member 100 to joint 200.

In another aspect, upper left frame 104 can be integral with upper right frame 106, and lower left frame 114 can be integral with lower right frame 116. In this aspect, a joint axle can slide transversely into joint aperture 108 during assembly of variable height structure 10. In this aspect, the connection between joint aperture 108 and joint 200 can be a pin connection to rotatably fix support member 100 to joint 200.

Support member 100 can include an upper longitudinal surface 124 and a lower longitudinal surface 126. Support member 100 can include a thickness $T_{sm}$ from lower longitudinal surface 126 to upper longitudinal surface 124. In an aspect, $T_{sm}$ can be approximately 6 mm.

The side portions of support member 100 can include an outer wall 120 and an inner wall 122. In an aspect, support member 100 can include a central aperture 130 that surrounds an aperture lumen 132. Aperture lumen 132 can be chamfered to receive a flexible conduit. In an aspect, aperture lumen 132 can have a diameter D, for example of approximately 5 mm.

Central aperture 130 can be connected to inner wall 122 by one or more aperture supports 140. One or more aperture supports 140, inner wall 122, and central aperture 130 can form an interior cell 142.

Joint 200 is shown in FIGS. 4-5. Each of joints 200a-i (and other joints) can have a structure as shown in FIGS. 4-5 with respect to joint 200, and as described below.

In an aspect, joint 200 can be a gimbal (e.g., a multi-axis gimbal, such as a two-axis gimbal). Joint 200 can rotate about a longitudinal axis y-y. For example, joint 200 can rotate relative to support member 100 along a longitudinal axis y-y. A portion of variable height structure 10 can rotate relative to joint 200 about a transverse axis x-x. For example, an expansion link 300 can rotate relative to joint 200 about a transverse axis x-x.

Joint 200 can include a body 202. Body 202 can include an upper face 204 and a lower face 206. An upper axle 232 can be connected to upper face 204. A lower axle 234 can be connected to lower face 206. As discussed above, upper axle 232 and lower axle 234 can extend into joint aperture 108 so joint 200 can rotate relative to support member 100 along longitudinal axis y-y. In another aspect, upper face 204 can be positioned adjacent upper left frame 104 and upper right frame 106 and lower face 206 can be positioned adjacent lower left frame 114 and lower right frame 116 (FIGS. 2-3). In an aspect, lower axle 234 and upper axle 232 can be integral to body 202. In another aspect, lower axle 234 can be integral to upper axle 232, but separately formed from body 202. In this aspect, body 202 can include an aperture to receive integral lower axle 234 and upper axle 232 (not shown).

A portion of body 202 can be positioned within an interior area of end cavity 110 of support member 100 (FIGS. 2-3).

As shown in FIG. 4, a transverse cylinder 212 can be connected to body 202. Transverse cylinder 212 can further include a shoulder 214 and a bearing surface 210. Transverse cylinder 212 can have a diameter Dj2 and shoulder 214 can have a diameter Dj1. In an aspect, diameter Dj1 can be less than diameter Dj2.

In an aspect, the diameter Dj1 can be approximately half the width of expansion link 300. For example, diameter Dj1 can range from approximately 1 mm to approximately 6 mm, such as approximately 2 mm to approximately 5 mm (e.g., approximately 3 mm).

Diameter Dj2 can be larger than Dj1 and can be sufficiently bigger than Dj1 to act as a shoulder to bear on for an expansion link 300. However, diameter Dj2 may be less than the height of body 202. The height of body 202 can be limited by the total height of support member 100 because there may be sufficient material to form upper frames 104 and 106 and lower frames 114 and 116 that attach to the joint. In an aspect, diameter Dj2 can be approximately 20 percent larger than diameter Dj1. For example, diameter Dj2 can range from approximately 1.2 mm to approximately 7.2 mm, such as approximately 2.4 mm to approximately 6 mm (e.g., approximately 3.6 mm). In an aspect, Dj1 can be approximately 3 mm, and Dj2 can be approximately 3.5 mm.

In another aspect, expansion link 300 can connect to bearing surface 210 so expansion link 300 can rotate relative to joint 200 about transverse axis x-x. In an aspect, shoulder 214 can abut an expansion link 300.

In an aspect, joint 200 can include a channel 220 that extends through joint 200 in the transverse direction. Channel 220 can be configured to receive a fastener to retain one or more expansion links 300 on bearing surface 210.

Figure 6:
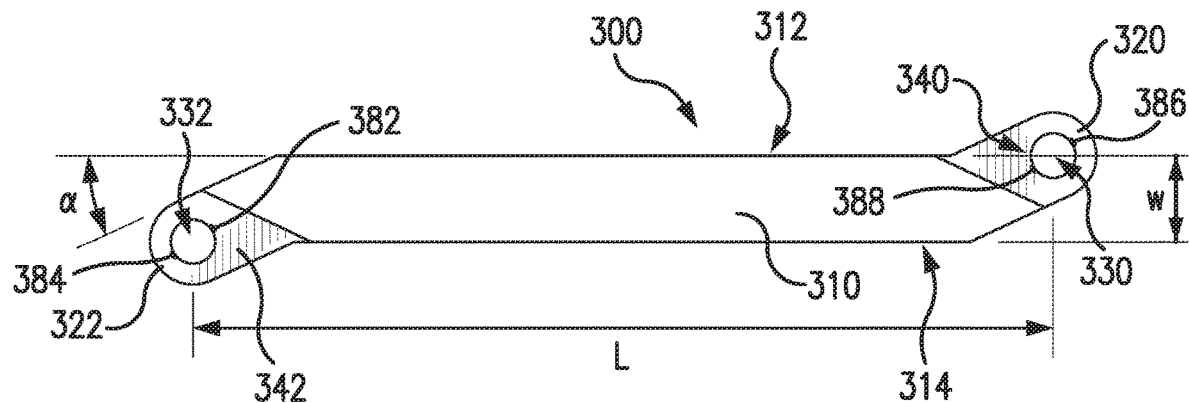
FIG. 6 is a front view of an expansion link for a variable height support structure.
Figure 7:
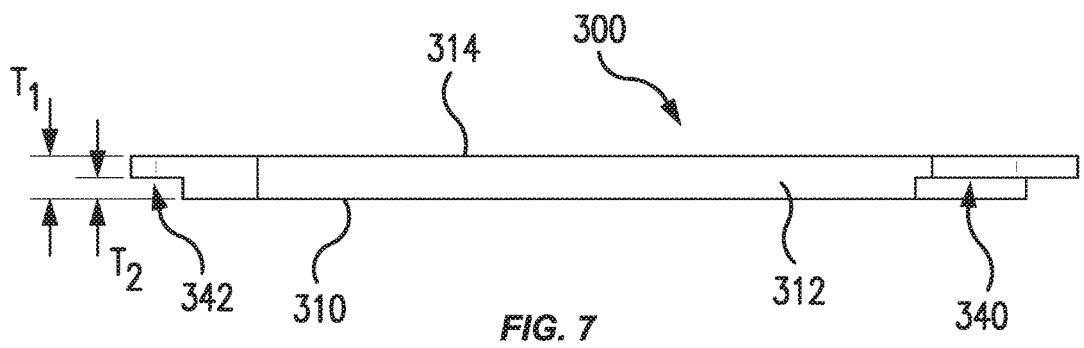
FIG. 7 is a top view of the expansion link of FIG. 6.
Figure 8:
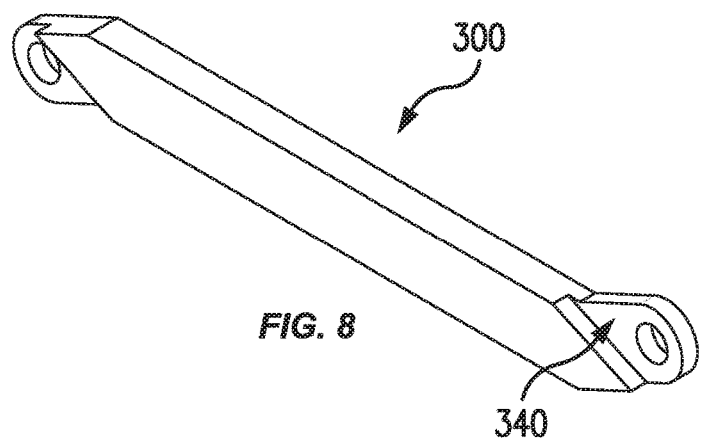
FIG. 8 is a perspective view of the expansion link of FIG. 6.

Expansion link 300 is shown in FIGS. 6-8. Each of expansion links 300a-f (and other expansion links) can have a structure as shown in FIGS. 6-8 with respect to expansion link 300, and as described below.

Expansion link 300 can have a front surface 310, an upper longitudinal surface 312, and a lower longitudinal surface 314. Expansion link 300 can have a first end 320 including a first link aperture 330. First end 320 can also include a first recessed surface 340. Expansion link 300 can have a length L. For example, length L can range from approximately 40 mm to approximately 80 mm, such as approximately 50 mm to approximately 70 mm (e.g., approximately 60 mm).

Expansion link 300 can have a second end 322 including a second link aperture 332. Second end 322 can include a second recessed surface 342. When positioned on variable height structure 10, first recessed surface 340 of a first expansion link 300 can abut second recessed surface 342 of an adjacent expansion link 300. For example, as shown in FIG. 1, first expansion link 300a can abut second recessed surface 342 of fourth expansion link 300d. First link aperture 330 and second link aperture 332 can surround a respective bearing surface 210 of joint 200 (FIGS. 4-5), to form bearings. For example, first link aperture 330 of first expansion link 300a can surround bearing surface 210 of joint 200a to form a first bearing, and second link aperture 332 of first expansion link 300a can surround bearing surface 210 of joint 200d to form a second bearing. In this aspect, the connection between each bearing surface 210 and each link aperture 332/334 can be a pin connection to rotatably fix an expansion link 300 to joint 200.

Expansion link 300 can have a thickness T1. Thickness T1 can range from approximately 1 mm to approximately 5 mm, such as approximately 2 mm to approximately 4 mm (e.g., approximately 3 mm). In an aspect, first recessed surface 340 and/or second recessed surface 342 can have a thickness T2. T2 can range from approximately 0.5 mm to approximately 2.5 mm, such as approximately 1 mm to approximately 2 mm (e.g., approximately 1.5 mm). Thickness T1 can be approximately 50% larger than thickness T2. For example, T1 can be approximately 3 mm, and T2 can be approximately 1.5 mm. Expansion link 300 can have a width W. In an aspect, width W can be approximately equal to thickness $T_{sm}$ of support member 100. For example, width W and thickness $T_{sm}$ can be approximately 6 mm.

First end 320 and/or second end 322 can be offset an angle alpha from upper longitudinal surface 312. In an aspect, alpha may range from approximately 5 degrees to approximately 90 degrees. For example, alpha may range from approximately 10 degrees to approximately 80 degrees. Alpha may range from approximately 15 degrees to approximately 35 degrees. Alpha may range from approximately 20 degrees to approximately 30 degrees. Alpha may be approximately 25 degrees.

Figure 9:
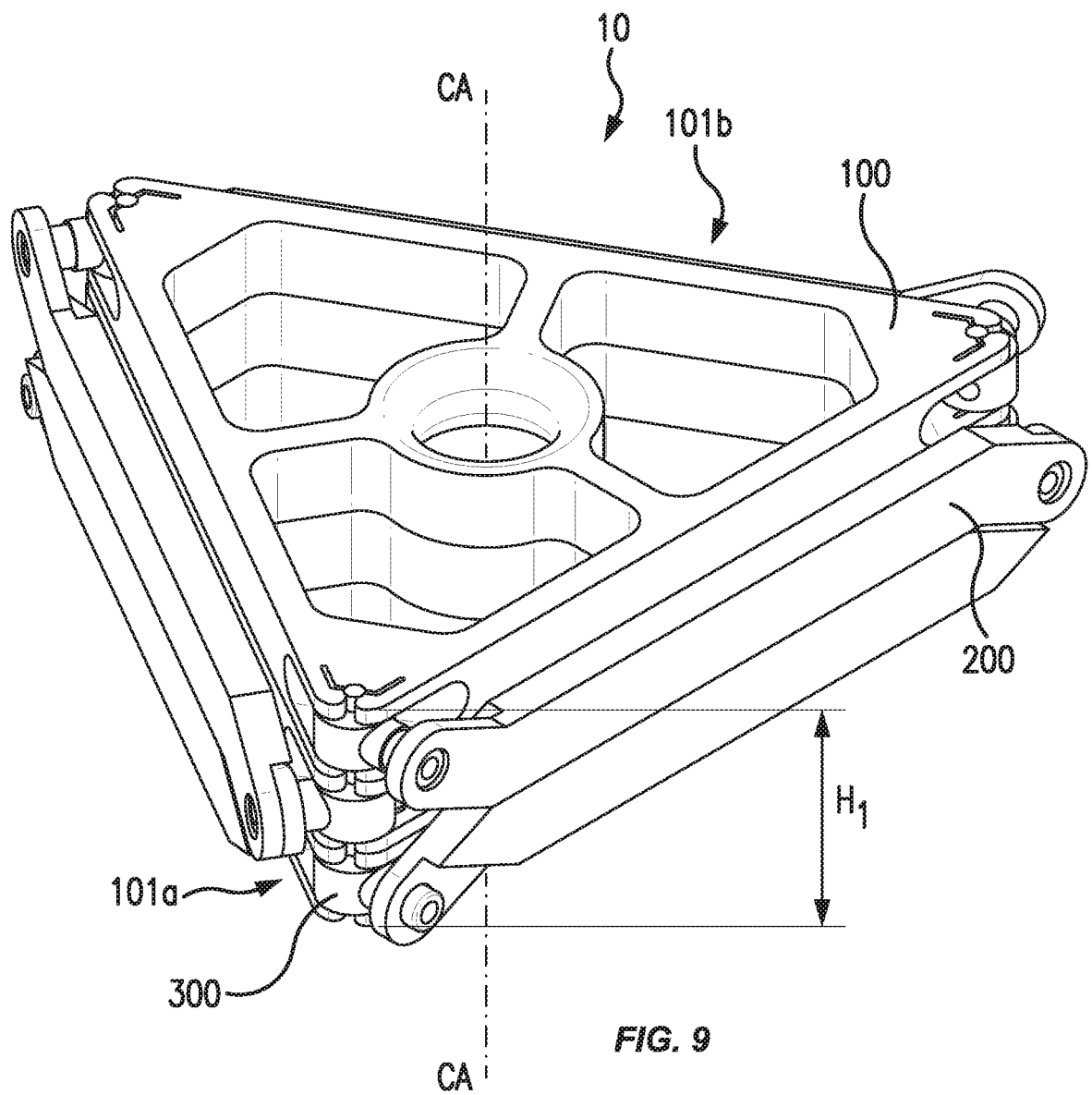
FIG. 9 is a perspective view of a variable height support structure in a compressed configuration.
Figure 10:
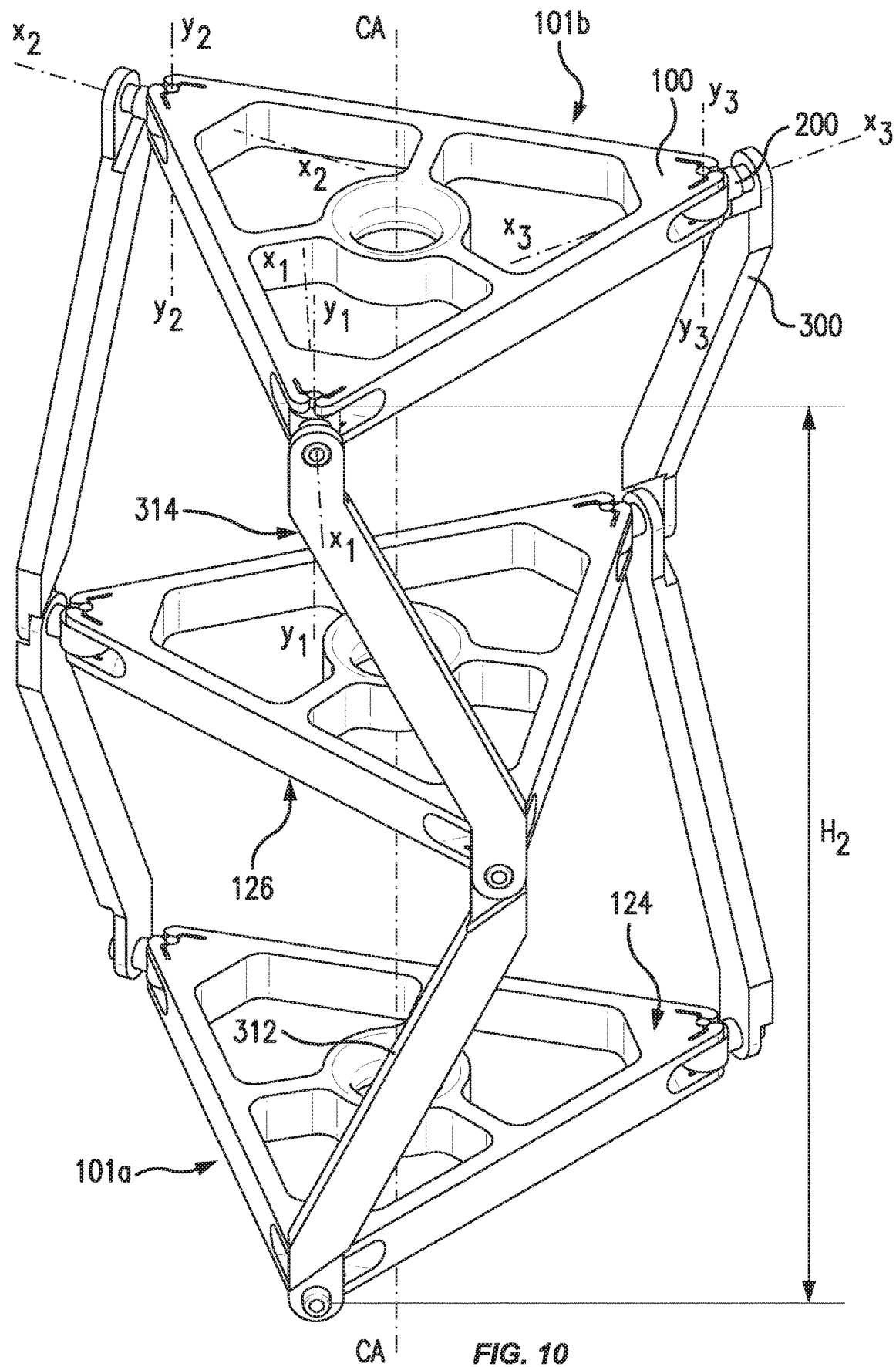
FIG. 10 is a perspective view of a variable height support structure in an expanded configuration.
Figure 11:
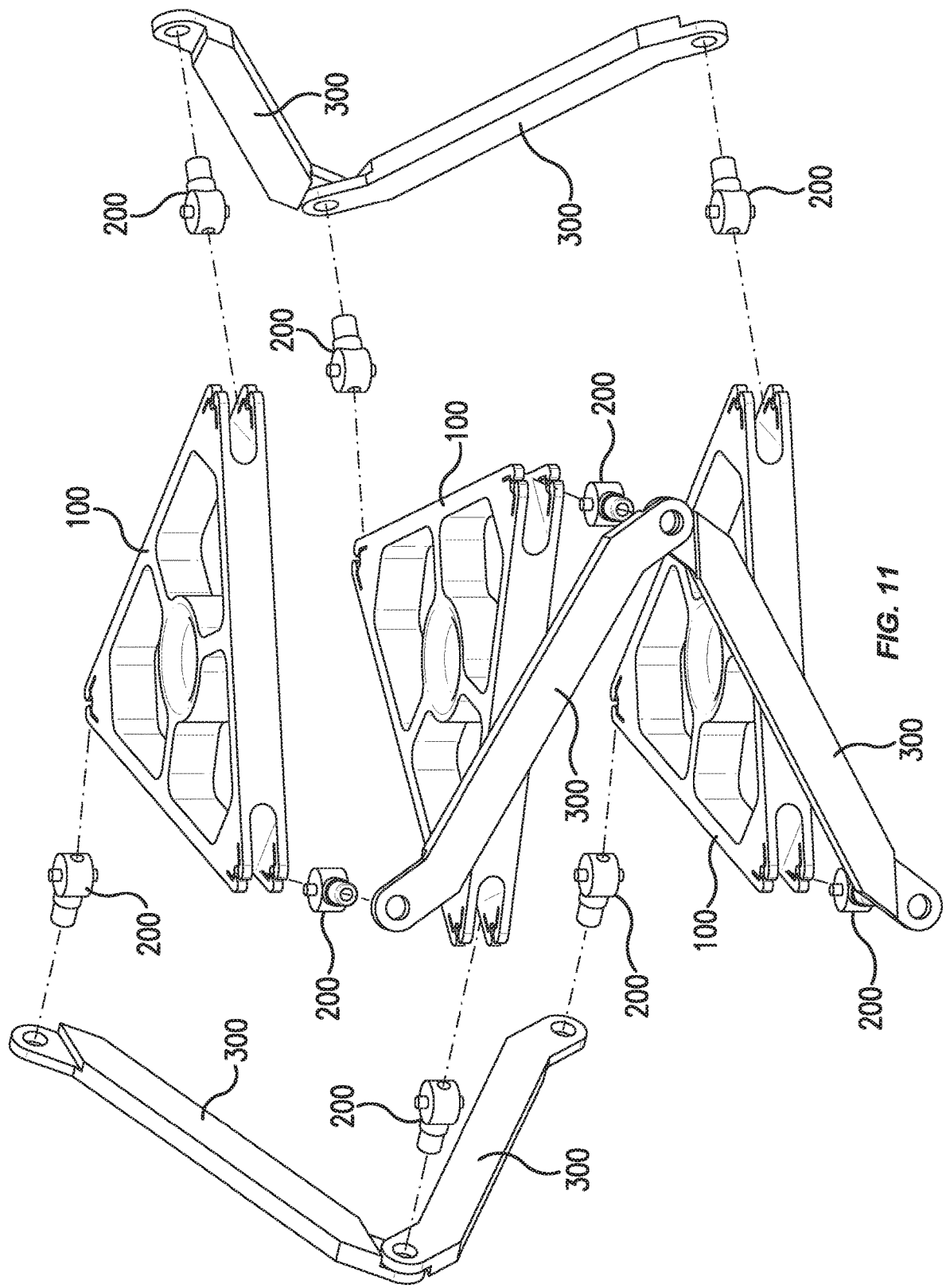
FIG. 11 is an assembly view of a variable height support structure.

Referring to FIGS. 9-11, variable height support structure 10 can selectively transition from a compressed configuration where adjacent support members 100 and/or adjacent expansion links 300 abut each other (FIG. 9) to an expanded configuration (FIG. 10). For example, variable height support structure can extend from a first end 101a to a second end 101b along a central longitudinal axis CA-CA. In the compressed configuration, an upper longitudinal surface 124 of a support member 100 can abut a lower longitudinal surface 126 of an adjacent support member 100. Additionally or alternatively, in the compressed configuration, an upper longitudinal surface 312 of one expansion link 300 can abut a lower longitudinal surface 314 of another expansion link 300. In some embodiments, there may be a small gap between adjacent support members 100 and/or between adjacent expansion links 300 when the variable height support structure 10 is in the compressed configuration.

In a compressed configuration for the variable height support structure 10 shown in FIG. 9, a height H1 of the variable height support structure 10 can be from lower longitudinal surface 126 of a support member 100 at first end 101a to an upper longitudinal surface 124 of a support member 100 at second end 101b along the central longitudinal axis CA-CA.

In the expanded configuration, an upper longitudinal surface 124 of a support member 100 can be spaced apart from a lower longitudinal surface 126 of an adjacent support member 100. In another aspect, in the expanded configuration, an upper longitudinal surface 312 of an expansion link 300 can be spaced apart from a lower longitudinal surface 314 of an expansion link 300.

In the expanded configuration for the variable height support structure 10 shown in FIG. 10, a height H2 of the variable height support structure 10 can be from lower longitudinal surface 126 of a support member 100 at first end 101a to an upper longitudinal surface 124 of a support member 100 at second end 101b along the central longitudinal axis CA-CA. In an aspect, the ratio of H2 to H1 is the expansion ratio of variable height support structure 10. The expansion ratio of variable height support structure 10 can be approximately 6.5 to 1. In an aspect, the expansion ratio of variable height support structure 10 can range from approximately 2 to 1 to approximately 10 to 1. The expansion ratio can range from approximately 3 to 1 to approximately 9 to 1. The expansion ratio can range from approximately 3 to 1 to approximately 8 to 1. The expansion ratio can range from approximately 4 to 1 to approximately 7 to 1.

The expansion ratio can be inversely proportional to the strength and stiffness of variable height structure 10. In addition, the length of each side of support member 100 relative to the thickness can be proportional to the expansion ratio. The expansion ratio can be optimized for each application by varying the thickness $T_{sm}$ of support member 100 and the length of each side.

In an aspect, the thickness of support member 100 can be minimized to achieve a high expansion ratio. There may be a trade-off between the possible size and strength of the bearing surface 210 (e.g., diameter Dj1) and the material of second end 322 of expansion link 300 around the bearing surface 210. In an aspect, the thickness $T_{sm}$ of support member 100 can be approximately 6 mm, which may allow the width W of expansion link 300 to also be approximately 6 mm without interfering with the other links. To balance the strength of the joint, the diameter Dj1 can be approximately half of the width of expansion link 300, for example 3 mm.

As shown in FIG. 10, a joint 200 can rotate about a first longitudinal axis y1-y1. For example, joint 200 can rotate relative to a support member 100 along a first longitudinal axis y1-y1 and longitudinal axis y1-y1 can be parallel to longitudinal central axis CA-CA. A portion of variable height structure 10 can rotate relative to joint 200 about a first transverse axis x1-x1. For example, an expansion link 300 can rotate relative to joint 200 about a first transverse axis x1-x1. Another joint 200 can rotate about a second longitudinal axis y2-y2. For example, joint 200 can rotate relative to a support member 100 along a second longitudinal axis y2-y2 and longitudinal axis y2-y2 can be parallel to longitudinal central axis CA-CA. A portion of variable height structure 10 can rotate relative to joint 200 about a second transverse axis x2-x2. For example, another expansion link 300 can rotate relative to joint 200 about a second transverse axis x2-x2. Another joint 200 can rotate about a third longitudinal axis y3-y3. For example, joint 200 can rotate relative to a support member 100 along a third longitudinal axis y3-y3 and longitudinal axis y3-y3 can be parallel to longitudinal central axis CA-CA. A portion of variable height structure 10 can rotate relative to joint 200 about a third transverse axis x3-x3. For example, another expansion link 300 can rotate relative to joint 200 about a third transverse axis x3-x3.

Overextension of variable height support structure could occur where support member 100, joint 200, and expansion link 300 continue moving beyond H2 and back toward a compressed configuration, but with adjacent surfaces of expansion links 300 being reversed. In an aspect, variable height support structure 10 can include one or more features to prevent overextension, For example, variable height support structure 10 can include a projection 280 on joint 200 (FIG. 4) that interfaces with stops 382/384 or 386/388 on expansion link 300 to prevent overextension (FIG. 5). In another aspect, variable height support structure 10 can include an elastic mechanism, such as a spring, to bias variable height support structure 10 to the compressed configuration to prevent overextension.

In an aspect, support member 100 can be connected to three joints and can have a triangular shape. In another aspect, support member can have any shape, so long as the shape intersects the three joints and does not restrict movement of the respective joints.

Figure 12:
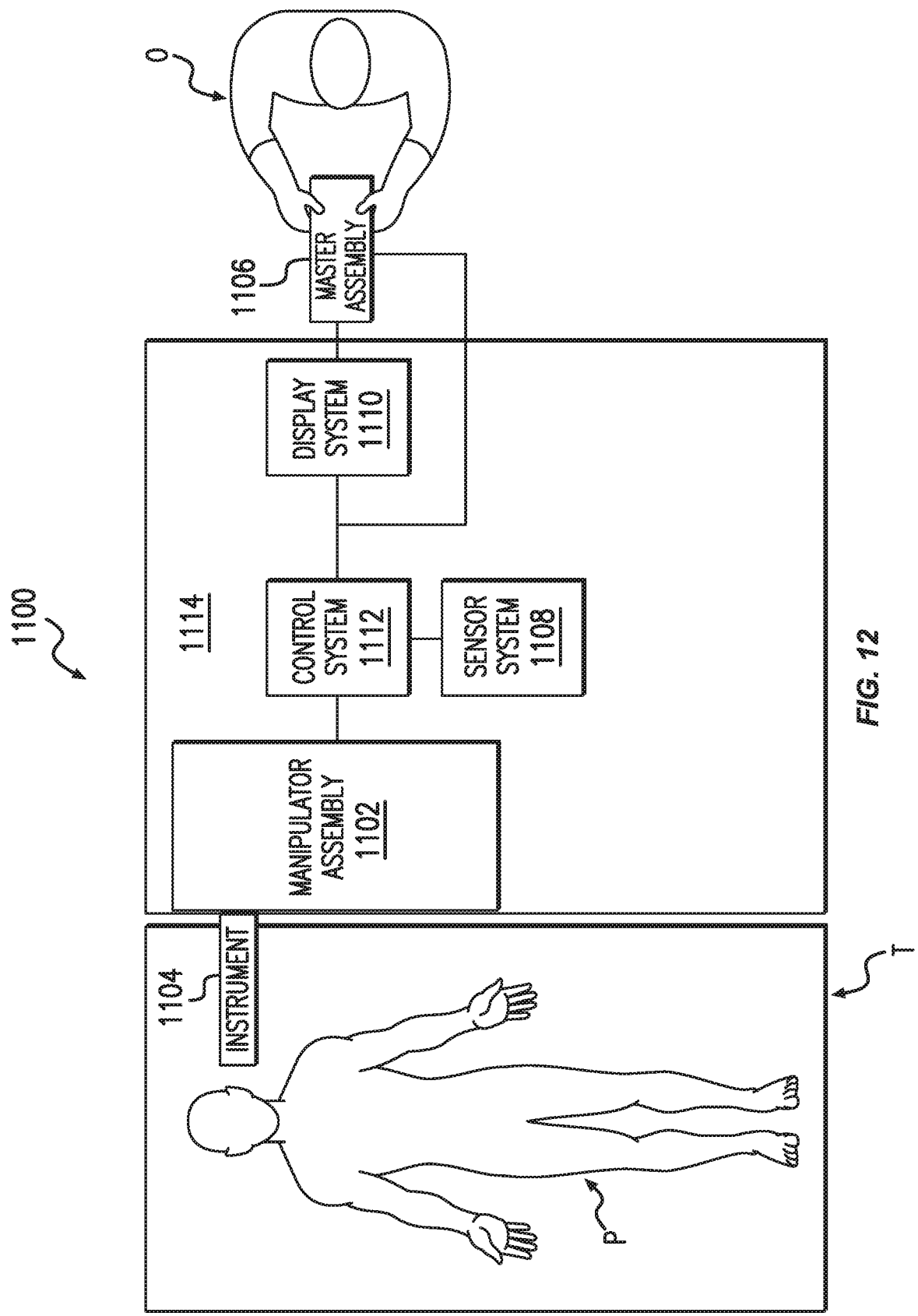
FIG. 12 is a simplified diagram of a medical system according to some embodiments.

As shown in FIG. 12, a medical system 1100 may include a manipulator assembly 1102 for operating a medical instrument 1104 in performing various procedures on a patient P. The manipulator assembly 1102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 1102 can be mounted to an operating table T, or to a main support 1114 (e.g., a cart, stand, second table, and/or the like). A master assembly 1106 allows an operator (e.g., a surgeon, a clinician, or a physician as illustrated in FIG. 12) to view the interventional site and to control manipulator assembly 1102.

Master assembly 1106 may be located at an operator console which may be located in the same room as operating table T, such as at the side of a surgical table on which patient P is located. However, it should be understood that operator O can be located in a different room or a completely different building from patient P. Master assembly 1106 may include one or more control devices for controlling manipulator assembly 1102. The control devices may include any number of a variety of input devices, such as joysticks, trackballs, scroll wheels, data gloves, trigger-guns, hand-operated controllers, voice recognition devices, body motion or presence sensors, and/or the like. To provide operator O a strong sense of directly controlling instruments 1104 the control devices may be provided with the same degrees of freedom as the associated medical instrument 110. In this manner, the control devices provide operator O with telepresence or the perception that the control devices are integral with medical instruments 1104.

In some embodiments, the control devices may have more or fewer degrees of freedom than the associated medical instrument 1104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 1102 supports medical instrument 1104, and may include a kinematic structure of one or more non-servo controlled links (e.g., one or more links that may be manually positioned and locked in place, generally referred to as a set-up structure), and/or one or more servo controlled links (e.g., one or more powered links that may be controlled in response to commands from the control system), and a manipulator. Manipulator assembly 1102 may optionally include a plurality of actuators or motors that drive inputs on medical instrument 1104 in response to commands from the control system (e.g., a control system 1112). The actuators may optionally include drive systems that when coupled to medical instrument 1104 may advance medical instrument 1104 into a naturally or surgically created anatomic orifice. Other drive systems may move the distal end of medical instrument 1104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 1104 for grasping tissue in the jaws of a biopsy device and/or the like. Actuator position sensors such as resolvers, encoders, potentiometers, and other mechanisms may provide sensor data to medical system 1100 describing the rotation and orientation of the motor shafts. This position sensor data may be used to determine motion of the objects manipulated by the actuators.

Medical system 1100 may include a sensor system 1108 with one or more sub-systems for receiving information about the instruments of manipulator assembly 1102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 1104; and/or a visualization system for capturing images from the distal end of medical instrument 1104.

Medical system 1100 may also include a display system 1110 for displaying an image or representation of the surgical site and medical instrument 1104 generated by sub-systems of sensor system 1108, recorded pre-operatively or intra-operatively using image data from imaging technology and/or a real time image such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, endoscopic images, and/or the like. The pre-operative or intra-operative image data may be presented as two-dimensional, three-dimensional, or four-dimensional (including, e.g., time-based or velocity-based information) images and/or as images from models created from the pre-operative or intra-operative image data sets. Display system 1110 and master assembly 1106 may be oriented so operator O can control medical instrument 1104 and master assembly 1106 with the perception of telepresence.

Medical system 1100 may also include control system 1112. Control system 1112 includes at least one memory and at least one computer processor (not shown) for effecting control between medical instrument 1104, master assembly 1106, sensor system 1108, and display system 1110. Control system 1112 also includes programmed instructions (e.g., a non-transitory machine-readable medium storing the instructions) to implement some or all of the methods described in accordance with aspects disclosed herein, including instructions for providing information to display system 1110. While control system 1112 is shown as a single block in the simplified schematic of FIG. 12, the system may include two or more data processing circuits with one portion of the processing optionally being performed on or adjacent to manipulator assembly 1102, another portion of the processing being performed at master assembly 1106, and/or the like. The processors of control system 1112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the systems described herein. In one embodiment, control system 1112 supports wireless communication protocols such as Bluetooth, IrDA, HomeRF, IEEE 802.11, DECT, and Wireless Telemetry.

In some embodiments, control system 1112 may receive force and/or torque feedback from medical instrument 1104. Responsive to the feedback, control system 1112 may transmit signals to master assembly 1106. In some examples, control system 1112 may transmit signals instructing one or more actuators of manipulator assembly 1102 to move medical instrument 1104. Medical instrument 1104 may extend into an internal surgical site within the body of patient P via openings in the body of patient P. Any suitable conventional and/or specialized actuators may be used. In some examples, the one or more actuators may be separate from, or integrated with, manipulator assembly 1102. In some embodiments, the one or more actuators and manipulator assembly 1102 are provided as part of a teleoperational cart positioned adjacent to patient P and operating table T.

Control system 1112 may optionally further include a virtual visualization system to provide navigation assistance to operator O when controlling medical instrument 1104 during an image-guided surgical procedure. Virtual navigation using the virtual visualization system may be based upon reference to an acquired preoperative or intraoperative dataset of anatomic passageways.

During a virtual navigation procedure, sensor system 1108 may be used to compute an approximate location of medical instrument 1104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system. For example, PCT Publication WO 2016/191298 (published Dec. 1, 2016) (disclosing "Systems and Methods of Registration for Image Guided Surgery"), which is incorporated by reference herein in its entirety, discloses such one system. Various systems and methods for monitoring the shape and relative position of an optical fiber in three dimensions are described in U.S. patent application Ser. No. 11/180,289 (filed Jul. 12, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,289,187 (filed on Jun. 17, 1998) (disclosing "Optical fibre bend sensor"), which are all incorporated by reference herein in their entireties.

Medical system 1100 may further include optional operations and support systems (not shown) such as illumination systems, steering control systems, irrigation systems, and/or suction systems. In some embodiments, medical system 1100 may include more than one manipulator assembly and/or more than one master assembly. The exact number of manipulator assemblies may depend on the surgical procedure and the space constraints within the operating room, among other factors. Master assembly 1106 may be collocated or they may be positioned in separate locations. Multiple master assemblies allow more than one operator to control one or more manipulator assemblies in various combinations.

In some embodiments, the manipulator assembly 1102, control system 1112, sensor system 1108, and display system 1110 may all be supported by support structure 1114 or may be integrated into support structure 1114. Alternatively, one or more components (e.g., manipulator assembly 1102, control system 1112, sensor system 1108, and/or display system 1110) may be mounted to the operating table T or integrated into the master assembly 1106.

Figure 13:
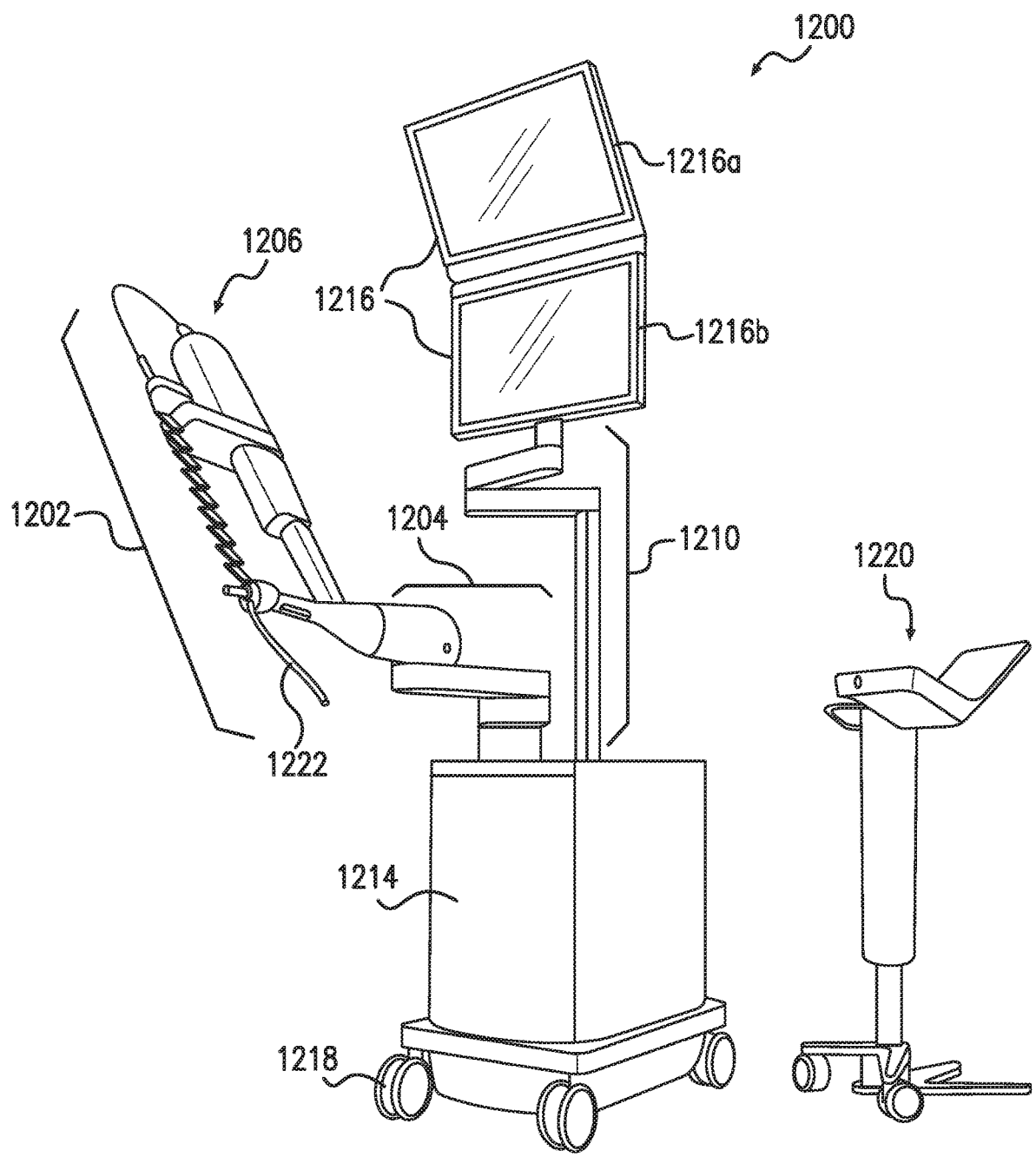
FIG. 13 illustrates various aspects of a medical system according to some embodiments.

FIG. 13 illustrates, as an example of a medical system 1100, a medical system 1200 according to an embodiment of the present disclosure. Medical system 1200 can include a master control 1220 and a system cart 1214 which supports a manipulator assembly 1202 and a display system 1216. The manipulator assembly can be configured to support and position an elongate device such as elongate device 1222. Various elongate devices are described in PCT/US18/43041 (filed Jul. 20, 2018) (disclosing "Flexible elongate device systems and methods"), which is incorporated by reference herein in its entirety.

The system cart 1214 is mounted on a set of wheels 1218 to allow positioning of the system cart 1214 at a desired location relative to an operating table (e.g., operating table T) and the patient (e.g., patient P). The system cart 1214 also supports display system 1216 which includes monitor support arm 1210, and display monitors 1216a, 1216b. Monitor support arm 1210 includes multiple links and joints which provide adjustable positioning of display monitors 1216a and 1216b in the vertical and lateral directions, as well as rotationally about a vertical axis relative to the system cart 1214, to position either monitor 1216a, 1216b at a desired viewing angle from the operator's point of view. Display system 1216 may provide for up to 360 degree rotation, e.g. 0-180 degrees rotation, of monitor 1216a about a horizontal axis allowing monitor 1216a to be positioned at a desired viewing angle or be folded and stowed in a collapsed configuration against monitor 1216b for storage. Various systems and methods relating to a system cart and monitors are described in PCT/US18/12995 (filed Jan. 9, 2018) (disclosing "Systems and methods for using a robotic medical system"), which is incorporated by reference herein in its entirety. The system cart 1214 may include hardware (e.g., processor(s), firmware) and/or or software to perform functions for performing shape-sensing with respect to a flexible elongate device.

The medical system 1200 of FIG. 13 also includes a master control 1220 according to one embodiment, some aspects of which are discussed above with respect to master assembly 1106. The master control 1220 may include various input controls for an operator (e.g., operator O, FIG. 12) to use for interactively controlling operations of the manipulator assembly 1202, for example functions performed by the instrument manipulator 1206. In some embodiments, the master control 1220 includes a scroll wheel and a trackball. In an example implementation, the scroll wheel may be rolled forwards or backwards in order to control the advancement or retraction of a medical instrument (e.g., elongate device 1222) with respect to the patient anatomy, and the trackball may be rolled in various directions by an operator in order to steer the position of the distal end portion and/or distal tip of the elongate device 1222, for example to control bend or articulation. Various systems and methods related to motion control consoles are described in PCT/US18/44419 (filed Jul. 30, 2018) (directed to "Systems and methods for safe operation of a device") and U.S. patent application Ser. No. 16/049,640 (filed Jul. 30, 2018) (disclosing "Systems and methods for steerable elongate device"), which are incorporated by reference herein in their entireties.

Figure 14:
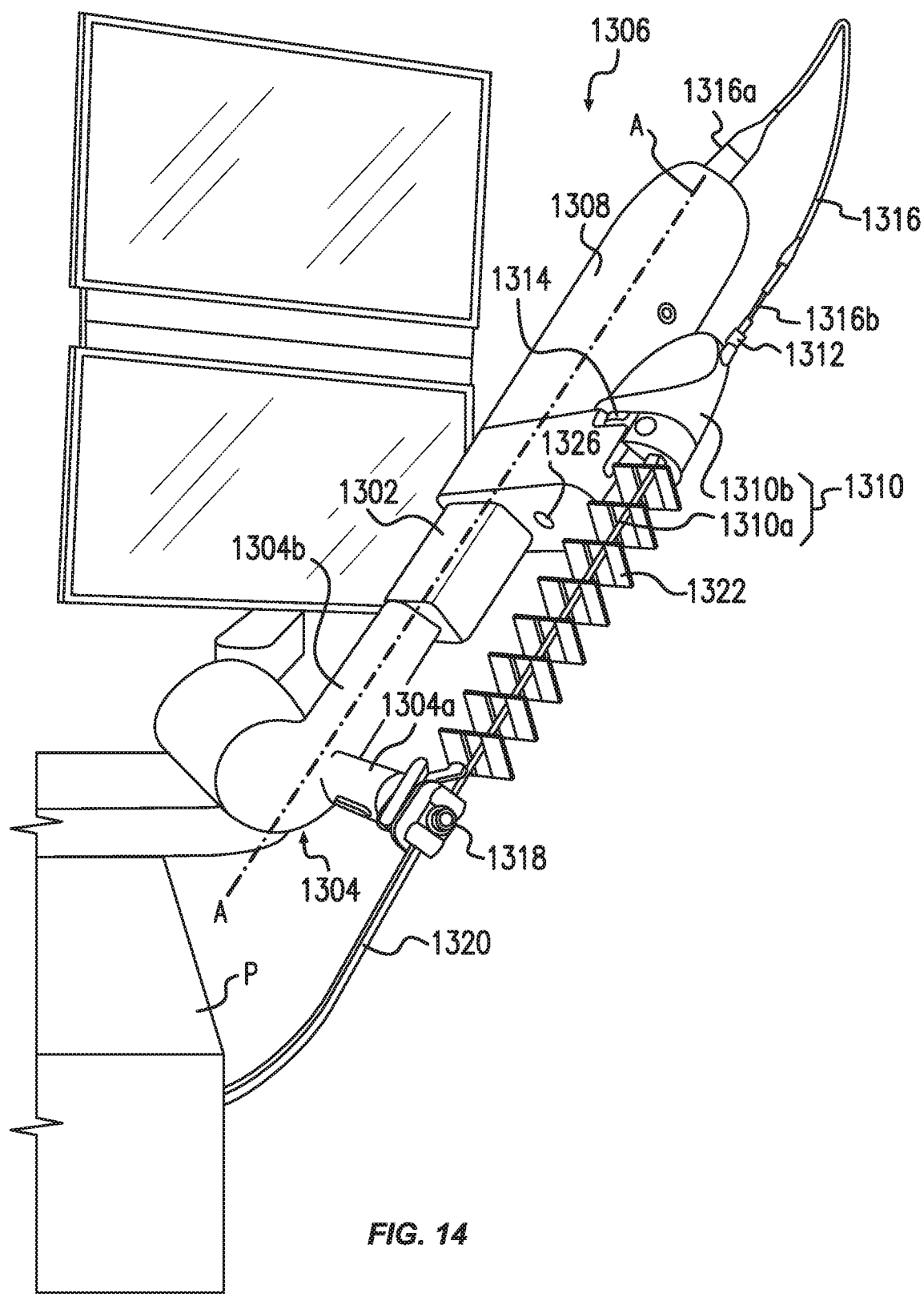
FIGS. 14 and 15 illustrate various aspects of an instrument manipulator according to some embodiments.
Figure 15:
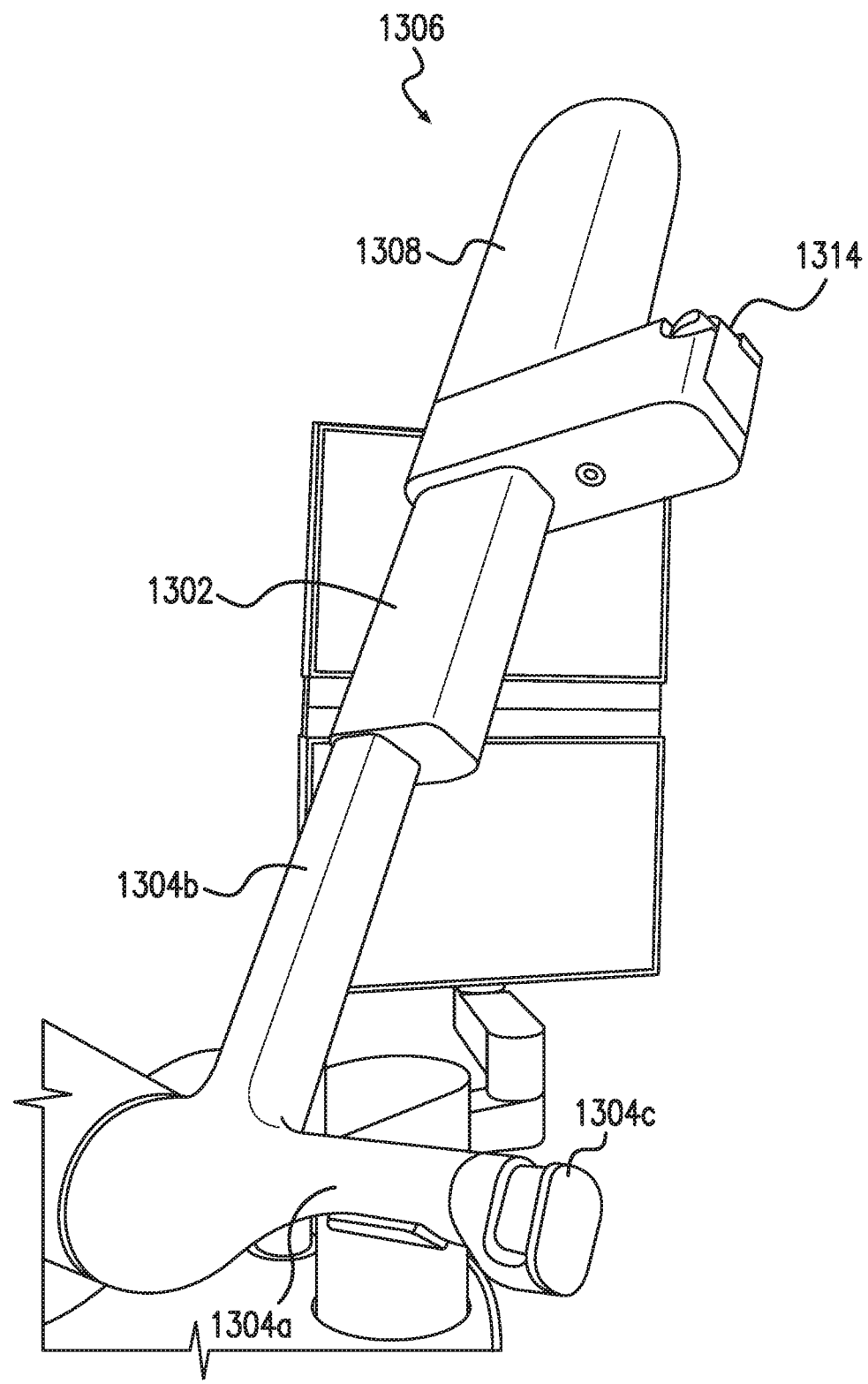

FIGS. 14 and 15 illustrate an example of an instrument manipulator 1306, which can be substantially similar to instrument manipulator 1206. The instrument manipulator 1306 includes a base 1304, an insertion stage 1302, and an instrument carriage 1308 to which an elongate device assembly 1310, is coupled. The instrument manipulator 1306 provides for insertion and retraction of the elongate device assembly 1310, with respect to the patient anatomy, by moving the instrument carriage 1308 and insertion stage 1302 in a telescoping manner relative to base 1304 and along the linear axis A. The base 1304 includes a shaft portion 1304a and main portion 1304b. As will be described in greater detail below, the shaft portion 1304a removably couples to a device connector 1318 which receives the elongate device 1310a. The insertion stage 1302 is coupled to the main portion 1304b of the base 1304 and translates along the main portion 1304b. The instrument carriage 1308 is coupled to and translates along the insertion stage 1302. As shown, the insertion stage 1302 and instrument carriage 1308 have respective protective coverings and/or and housings, and when the instrument manipulator 1306 is moved along the axis A, the respective coverings and/or housings at least partially overlap with each other, thereby effecting a telescoping effect, to facilitate sealing and optimal slidable fit.

The elongate device assembly 1310 can include an elongate device 1310a and a control assembly 1310b. The instrument carriage 1308 couples to control assembly 1310b at an instrument interface 1314 of the instrument carriage 1308. The instrument manipulator 1306 also couples to a probe assembly 1316 which includes a probe 1316b and a probe connector 1316a. The probe assembly 1316 may insert into a working lumen of the elongate device 1310a through the connector 1312 on the control assembly 1310b and may run through the elongate device 1310a. The probe 1316b may include a viewing scope assembly that records concurrent or real-time images of a surgical site and provides the images to an operator (e.g., operator O, FIG. 12) through one or more displays (e.g., one or more displays of display system 1110 in FIG. 12). The instrument carriage 1308 may include electronic and optical components providing probe 1316b endoscopic capabilities. In some embodiments, the probe assembly 1316 may be detached from the instrument manipulator 1306 and elongate device control assembly 1310b, and removed from elongate device assembly 1310. Alternative instruments such as biopsy needles, ablation tools, and other flexible instruments may be coupled to instrument manipulator 1306 and/or elongate device assembly 1310, through the elongate device 1310 working lumen.

A device connector 1318 can include a manipulator interface which can be removeably coupled to distal end portion 1304c of base 1304, a distal end which can be removeably coupled to a patient medical device 1320, and a proximal end which can receive elongate device 1310a. The patient medical device 1320 (such as an endotracheal tube, a laryngeal mask airway, a cannula, etc.) can be fixed to patient anatomy to facilitate insertion of various medical devices into patient anatomy. For example, the patient medical device 1320 may be an endotracheal tube inserted into the mouth and trachea of the patient P to help provide mechanical ventilation for the patient P and to provide a conduit for the elongate device 1310a to be navigated within the lungs of the patient P to facilitate imaging, biopsy, and/or treatment. Various systems and methods related to device connectors are described in PCT/US2018/017085 (filed Feb. 6, 2018) (disclosing "Systems and methods for coupling components of a medical system"), which is incorporated by reference herein in its entirety. In some embodiments, the elongate device 1310a runs through an elongate device guide 1322, which is a selectively collapsible and extendable device that supports the length of the elongate device 1310a during movement of the instrument carriage 1308. In an aspect, variable height support structure 10 can be elongate device guide 1322. Various systems and methods related to catheter guides such as elongate device guides are described in PCT/US2017/041160 (filed Jul. 7, 2017) (disclosing "Guide apparatus for delivery of an elongate device and methods of use"), which is incorporated by reference herein in its entirety.

Figure 16A:
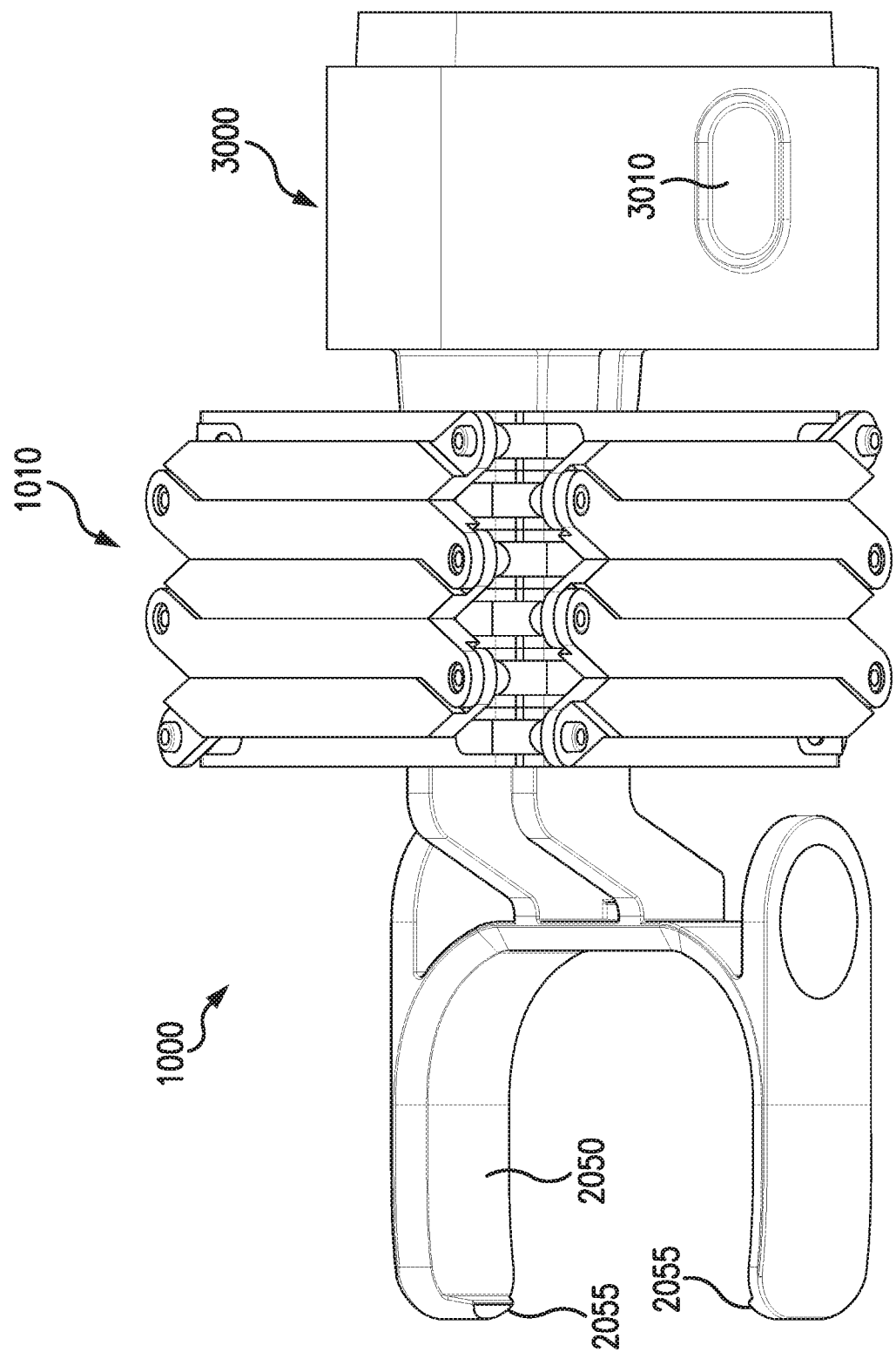
FIGS. 16A and 16B illustrate perspective views of an illustrative instrument guiding apparatus according to some embodiments.
Figure 16B:
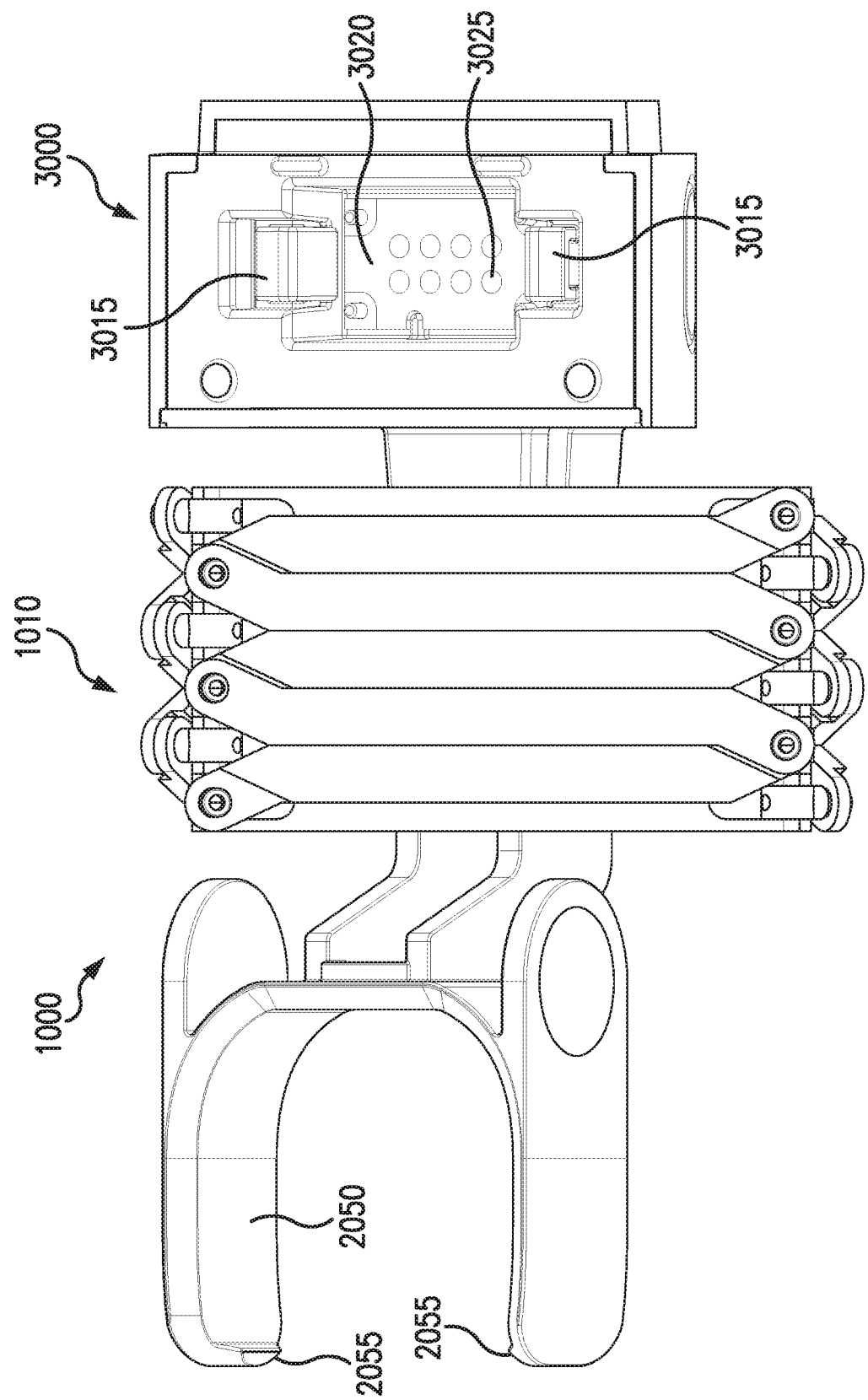

FIGS. 16A-16B illustrate perspective views of an illustrative instrument guiding apparatus 1000 according to some embodiments of the present disclosure. Instrument guiding apparatus 1000 can include a variable-length support assembly 1010. Variable-length support assembly 1010 can be substantially similar to variable-length support structure 10 described herein. FIG. 16A displays the instrument guiding apparatus 1000 from a top perspective while FIG. 16B displays the instrument guiding apparatus 1000 from a bottom perspective.

The instrument guiding apparatus 1000 may include one or more couplers for coupling the instrument guiding apparatus 1000 to an instrument manipulator. For example, the instrument guiding apparatus 1000 may include a proximal coupler 3000. The proximal coupler 3000 may include mechanical fasteners, such as latches, mounting screws, magnetic connections, etc. for detachably coupling the proximal end of the instrument guiding apparatus 1000 to an assembly such as manipulator assembly 1102 of medical system 1100, manipulator assembly 1202 of medical system 1200, or instrument manipulator 1306. The proximal coupler 3000 may include an enclosure that can provide a housing for electronics such as printed circuit boards (PCBs) and/or sensors associated with the instrument guiding apparatus 1000. For example, an instrument guiding apparatus PCB 3020 may be provided with electrical pads 3025 configured to mate with corresponding pins (e.g., pogo pins) on a system PCB (not shown) provided on the manipulator assembly 1102. A controller within the medical system 1100 can monitor and count a frequency of connecting and disconnecting the pogo pins with the system PCB in order to determine the number of times instrument guiding apparatus 1000 is mounted to the manipulator assembly 1102. In an alternative embodiment, the PCB can be replaced with a presence sensor indicating installation and/or removal of the instrument guiding apparatus 1000. In some embodiments, the presence sensor may be a life cycle indicator if the instrument guiding apparatus 1000 has a limited number of life cycles. The controller can save the number of connections of instrument guiding apparatus 1000 and provide an indication to the user when a new instrument guiding apparatus 1000 is to be used for a next medical procedure. In one example, the support assembly PCB can include identification information and the controller can record a number of uses of the instrument guiding apparatus 1000 correlated to a specific identification part number representing the specific instrument guiding apparatus 1000.

The proximal coupler 3000 may include a coupling mechanism for detachably coupling an end of the instrument guiding apparatus 1000 to the manipulator assembly 1102 or other manipulator assemblies (not shown). In the illustrated embodiment of FIGS. 16A and 16B, the housing may include a pair of latches 3015 which can be actuated with buttons 3010 positioned on the outer surface of the proximal coupler 3000. The buttons may be depressed to compress the latches to mate with corresponding attachment elements (not shown) on the manipulator assembly 1102. In alternative embodiments the coupling mechanism may include any type of fastening element such as snap-fit engagements, frictional engagements, hook-and-eye fasteners, pins, magnetic fasteners, bolts (e.g., carriage bolts), screws (e.g., mating screws, thumb screws), and/or the like.

As illustrated in FIGS. 16A and 16B, a distal coupler 2050 may also be provided to detachably couple the distal end of the instrument guiding apparatus 1000 to a portion of the manipulator assembly 1102 such as a support arm included within the manipulator assembly 1102 (not shown). Similarly, the distal coupler 2050 may detachably couple the distal end of the instrument guiding apparatus 1000 to the shaft portion 1304a of the instrument manipulator 1306 shown in FIG. 14. The distal coupler 2050 may include a C-shaped clamp constructed from a flexible material which can flex open with pressure to be installed onto the support arm and return to an original shape to lock onto the support arm. The support arm may include slots (not shown) which can mate with protrusions 2055 on the distal coupler 2050.

In alternative embodiments, the enclosure may be included on the distal end of the instrument guiding apparatus 1000 only or on both the distal and proximal ends of the instrument guiding apparatus 1000. Alternatively, a coupler such as illustrated in FIG. 16A may be included on the distal and/or proximal ends of instrument guiding apparatus 1000. Additionally, while the proximal coupler 3000 is illustrated in FIG. 16A with respect to instrument guiding apparatus 1000, it should be understood that the proximal coupler 3000, electronics, mechanical fasteners, and controllers for counting of variable-length support assembly life cycles can be implemented within any embodiments of instrument guiding apparatus including but not limited to instrument guiding apparatus 1000.

In some embodiments, shape-sensing may be used, in conjunction with the rotation of a manipulator assembly as in accordance with embodiments described above, to determine the bend angle of the distal end of an elongate device such as a steerable, flexible catheter and ensure that the instrument manipulator is positioned at an angle of inclination that is optimal for aligning the elongate device with an axis of insertion into the patient anatomy. The determination can be performed to assess, based on the sensed shape of the distal end of the elongate device and the angle of inclination of the manipulator assembly, whether the bend of the distal end of the elongate device is oriented such that it is in, or is approaching, a problematic configuration that could have negative effects such as creating excessive friction in an endotracheal tube (e.g., endotracheal tube 1320) or could cause disengagement of a device connector (e.g., device connector 1318).

A control system (e.g., control system 1112, FIG. 12) with a memory and one or more programmable processors may be implemented to receive shape-sensing data from a shape-sensing system, indicating the shape along the length of the elongate device, and to receive data corresponding to the angle of inclination of the instrument manipulator, in order to make a determination, as described above, whether the bend of the distal end of the elongate device is in or is approaching a problematic configuration. The bend or other aspects of the orientation of the distal end of the elongate device and/or relative orientation of the instrument manipulator may be processed by comparing corresponding data to a threshold level or value. The control system may also be configured to, in response to the determination, output a visual indicator such as a colored light (e.g., red or green), a numerical value, a visual representation of the bend, or another type of visual indication that corresponds to, for example, whether there is a problematic relative orientation or not. The visual indicator may be displayed on a display system (e.g., display system 1110, FIG. 12). Various systems and methods for monitoring the shape and relative position of an optical fiber are described in U.S. patent application Ser. No. 11/180,289 (filed Jul. 12, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,289,187 (filed on Jun. 17, 1998) (disclosing "Optical fibre bend sensor"), which are all incorporated by reference herein in their entireties.

The examples above have been described with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described illustrative embodiments, but should be defined only in accordance with the following claims and their equivalents.

What is claimed is:

1. A variable height support structure for supporting a flexible elongate medical instrument, the variable height support structure comprising:
    a first support member connected to a first joint, a second joint, and a third joint, the first support member comprising a central aperture configured to receive and support the flexible elongate medical instrument;
    a second support member connected to a fourth joint, a fifth joint, and a sixth joint, the second support member comprising a central aperture configured to receive and support the flexible elongate medical instrument;
    a first expansion link connected to the first joint and the fourth joint;
    a second expansion link connected to the second joint and the fifth joint; and
    a third expansion link connected to the third joint and the sixth joint,
    wherein the variable height support structure selectively transitions from a compressed configuration to an expanded configuration while maintaining an alignment between the central aperture of the first support member and the central aperture of the second support member along a longitudinal central axis that extends between the central aperture of the first support member and the central aperture of the second support member.

2. The variable height support structure of claim 1, wherein the first joint further comprises a two-axis gimbal such that the two-axis gimbal rotates relative to the first support member along a longitudinal axis parallel to the longitudinal central axis and the first expansion link rotates about the two-axis gimbal along a transverse axis.

3. The variable height support structure of claim 2, wherein the second joint further comprises a second two-axis gimbal such that the second two-axis gimbal rotates relative to the first support member along a second longitudinal axis parallel to the longitudinal central axis and the second expansion link rotates about the second two-axis gimbal along a second transverse axis.

4. The variable height support structure of claim 3, wherein the third joint further comprises a third two-axis gimbal such that the third two-axis gimbal rotates relative to the first support member along a third longitudinal axis parallel to the longitudinal central axis and the third expansion link rotates about the third two-axis gimbal along a third transverse axis.

5. The variable height support structure of claim 2, wherein the first joint further comprises an axle to connect the two-axis gimbal to the first support member, the axle extending along the longitudinal axis.

6. The variable height support structure of claim 1, wherein the variable height support structure has an expansion ratio of approximately 6.5 to 1.

7. The variable height support structure of claim 1, wherein movement of the first support member, the second support member, the first expansion link, the second expansion link, and the third expansion link is constrained by a single degree of freedom along the longitudinal central axis.

8. The variable height support structure of claim 1, further comprising:
- a third support member connected to a seventh joint, an eighth joint, and a ninth joint;
- a fourth expansion link connected to the fourth joint and the seventh joint, the fourth expansion link including a fourth link recessed surface at an end of the fourth expansion link connected to the fourth joint;
- a fifth expansion link connected to the fifth joint and the eighth joint; and
- a sixth expansion link connected to the sixth joint and the ninth joint,
- wherein the first expansion link includes a first link recessed surface at an end of the first expansion link connected to the fourth joint such that the first link recessed surface is adjacent to the fourth link recessed surface along a transverse axis.

9. The variable height support structure of claim 1, wherein the central aperture of the first support member comprises a chamfered lumen configured to receive the flexible elongate medical instrument and to provide lateral support to the flexible elongate medical instrument.

10. The variable height support structure of claim 1, further comprising a coupler to couple the variable height support structure to an instrument manipulator.

11. The variable height support structure of claim 1, wherein when the variable height support structure is in the compressed configuration, the first support member is at a first rotational orientation, and when the variable height support structure is in the expanded configuration, the first support member is at a second rotational orientation different from the first rotational orientation.

12. The variable height support structure of claim 1, wherein the first support member is configured to rotate about the longitudinal central axis.

13. The variable height support structure of claim 1, wherein the first support member is configured to rotate with respect to the second support member as the variable height support structure selectively transitions from the compressed configuration to the expanded configuration.

* * * * *

UNITED STATES PATENT AND TRADEMARK OFFICE
CERTIFICATE OF CORRECTION

| | |
|---|---|
| PATENT NO. | : 12,193,757 B2 |
| APPLICATION NO. | : 17/065840 |
| DATED | : January 14, 2025 |
| INVENTOR(S) | : Timothy D. Boucher |

Page 1 of 1

It is certified that error appears in the above-identified patent and that said Letters Patent is hereby corrected as shown below:

In the Specification

Column 11, Line 6, change "110" to -- 1104 --

Signed and Sealed this
Twenty-fifth Day of March, 2025

Coke Morgan Stewart
*Acting Director of the United States Patent and Trademark Office*